(12) United States Patent
Tsukagoshi (10) Patent No.: US 6,987,827 B2
(45) Date of Patent: Jan. 17, 2006

(54) APPARATUS AND METHOD FOR X-RAY COMPUTER TOMOGRAPHY

(75) Inventor: Shinsuke Tsukagoshi, Otawara (JP)

(73) Assignees: Kabushiki Kaisha Toshiba, Tokyo (JP); Toshiba Medical Systems Corporation, Otawara (JP)

( * ) Notice: Subject to any disclaimer, the term of this patent is extended or adjusted under 35 U.S.C. 154(b) by 104 days.

(21) Appl. No.: 10/798,435

(22) Filed: Mar. 12, 2004

(65) Prior Publication Data

US 2004/0190674 A1    Sep. 30, 2004

(30) Foreign Application Priority Data

Mar. 28, 2003    (JP)    ............................. 2003-091970

(51) Int. Cl.
*A61B 6/03* (2006.01)
*G06F 17/00* (2006.01)
*G01N 23/083* (2006.01)

(52) U.S. Cl. .................. 378/4; 378/15; 378/8; 378/901
(58) Field of Classification Search .................... 378/4, 378/15, 8, 901, 95; 382/131
See application file for complete search history.

(56) References Cited

U.S. PATENT DOCUMENTS

| | | | | |
|---|---|---|---|---|
| 5,651,043 A | * | 7/1997 | Tsuyuki et al. | 378/65 |
| 5,796,802 A | * | 8/1998 | Gordon | 378/8 |
| 6,185,271 B1 | * | 2/2001 | Kinsinger | 378/19 |
| 6,188,744 B1 | * | 2/2001 | Shinohara et al. | 378/8 |
| 6,195,409 B1 | * | 2/2001 | Chang et al. | 378/20 |
| 6,243,436 B1 | | 6/2001 | Hahn et al. | |
| 2002/0071599 A1 | | 6/2002 | Herget et al. | |
| 2002/0181646 A1 | | 12/2002 | Mehldau | |
| 2003/0023166 A1 | | 1/2003 | Frisa et al. | |

FOREIGN PATENT DOCUMENTS

| | | |
|---|---|---|
| EP | 0 485 999 | 5/1992 |
| JP | 2002-8008 | 1/2002 |
| JP | 2002-272729 | 9/2002 |

OTHER PUBLICATIONS

Adobe Photoshop "Cropping Images" excerpt of instructions; version 3.01, (c) 1989-1999 and (c) 1991-1998.*
Sakurada, et al., "Gynecological Applications of Helical CT Using SmartPrep" Jpn. J. Med. Imaging, vol. 18, No. 3 (1999) p131-138.*

* cited by examiner

*Primary Examiner*—David V. Bruce
*Assistant Examiner*—Krystyna Suchecki
(74) *Attorney, Agent, or Firm*—Oblon, Spivak, McClelland, Maier & Neustadt, P.C.

(57) ABSTRACT

An X-ray computed tomographic apparatus of the invention includes a display portion to display, on a screen, a scanogram related to a subject together with a quadrilateral frame line specifying a reconstruction range, an input portion to input a command to transform the frame line specifying the reconstruction range to a parallelogram or rotate the frame line specifying the reconstruction range, a gantry to perform scanning in a scan range corresponding to the reconstruction range, and a reconstruction portion to reconstruct image data related to plural slices, parallel to one another and included in the reconstruction range, slice-by-slice on the basis of projection data acquired by the scanning.

24 Claims, 10 Drawing Sheets

APPARATUS AND METHOD FOR X-RAY COMPUTER TOMOGRAPHY

CROSS-REFERENCE TO RELATED APPLICATIONS

This application is based upon and claims the benefit of priority from prior Japanese Patent Application No. 2003-091970, filed Mar. 28, 2003, the entire contents of which are incorporated herein by reference.

BACKGROUND OF THE INVENTION

1. Field of the Invention

The present invention relates to apparatus and method for the X-ray computed tomography.

2. Description of the Related Art

The X-ray computed tomographic apparatus (also referred to as the CT scanner) provides information of the subject in the form of images on the basis of the intensity of X-rays having passed through the subject, and plays an important role in many medical practices including diagnosis of illness, treatment and operation planning, etc. The advent of helical scan has made it possible to achieve wide-range data acquisition in a short time.

Figures 1A, 1B:
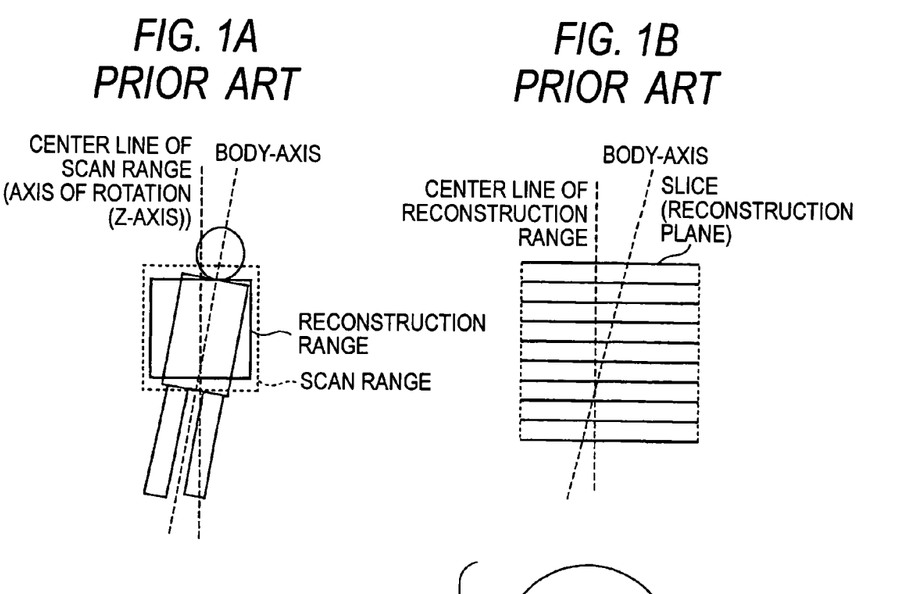
FIG. 1A, FIG. 1B, and FIG. 1C are views used to explain problems in the related art.
Figure 1C:
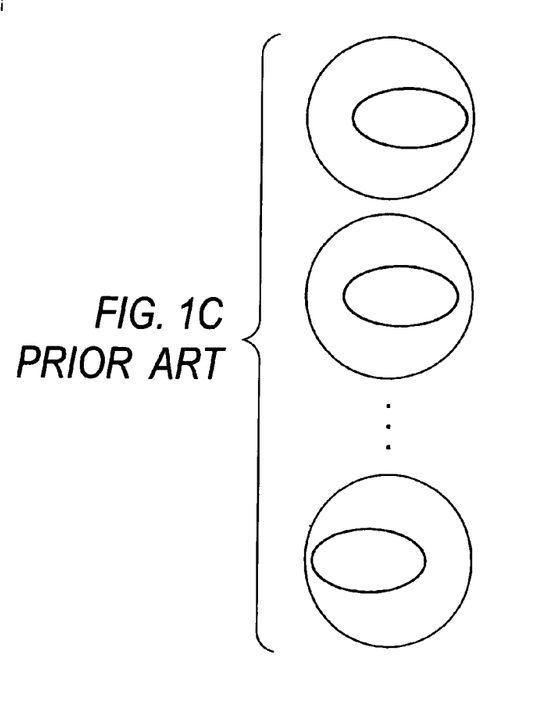

The patient throughput has become one of critical issues associated with such achievement. Due to ultrafast scans as well as weight saving of X-ray tubes, widespread use of helical scan, increasing number of detector arrays, and enhancement of detection sensitivity in recent years, the patient throughput is influenced more by a time needed for pre-scan setting of the subject than the scan time. The subject lies on his back on the tabletop of the diagnostic table and fine adjusts the body position according to radiologist's instructions. However, only a limited time is allowed for fine adjustment of the body position. Hence, as is shown in FIG. 1A, scans are often performed while the body axis of the subject is tilted with respect to the center line (Z-axis, the rotational axis of the X-ray tube) of the scan range. This results in an event that, as is shown in FIG. 1B and FIG. 1C, the center of the subject is offset from the center of the image and a degree of offset differs from image to image, which makes observations quite difficult.

BRIEF SUMMARY OF THE INVENTION

An object of the invention is therefore to address an event such that scans are performed while the body axis of the subject is tilted with respect to the center line (Z-axis, the rotational axis of the X-ray tube) of the scan range.

An X-ray computed tomographic apparatus of the invention includes: a display portion to display, on a screen, a scanogram related to a subject together with a quadrilateral frame line specifying a reconstruction range; an input portion to input a command to transform the frame line specifying the reconstruction range to a parallelogram or rotate the frame line specifying the reconstruction range; a gantry to perform scanning in a scan range corresponding to the reconstruction range; and a reconstruction portion to reconstruct image data related to plural slices, parallel to one another and included in the reconstruction range, slice-by-slice on the basis of projection data acquired by the scanning.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION

An embodiment of an X-ray computed tomographic apparatus of the invention will now be described with reference to the accompanying drawings. The X-ray computed tomographic apparatus includes various types, such as a rotate/rotate type in which a unit comprising the X-ray tube and the radiation detector rotates about the subject, and a stationary/rotate type in which a number of detection elements are aligned in a ring-shaped array and the X-ray tube alone rotates about the subject, and the invention is applicable to any type. Herein, the currently most popular rotate/rotate type will be described. Also, in order to reconstruct tomographic data for one slice, it is necessary to obtain projection data of about 360° for a full circle of the subject, and projection data of 180° plus a view angle is needed even in the half scan method. The invention is applicable to either reconstruction method. Herein, the former method will be described by way of example. Also, popular mechanisms to convert incident X-rays to charges are: an indirect conversion scheme,-by which X-rays are converted first into light by a fluorescent material, such as a scintillator, and the light is then converted to charges by a photoelectric converting element, such as a photodiode; and a direct conversion scheme, by which generation of electron-hole pairs in the semiconductor by X-rays and their movement to the electrodes, that is, the photoelectric phenomenon, are exploited. The X-ray detection elements adopting either scheme can be used, and herein, those adopting the former indirect conversion scheme will be described. In addition, a so-called multi-tube type X-ray computed tomographic apparatus, in which plural pairs of an X-ray tube and an X-ray detector are mounted to a rotational ring, has become commercially available recently, and the peripheral techniques are also under development. The invention is applicable to either a conventional single-tube type X-ray computed tomographic apparatus or a multi-tube type X-ray computed tomographic apparatus. Herein, a single-tube type X-ray computed tomographic apparatus will be described.

Figure 2:
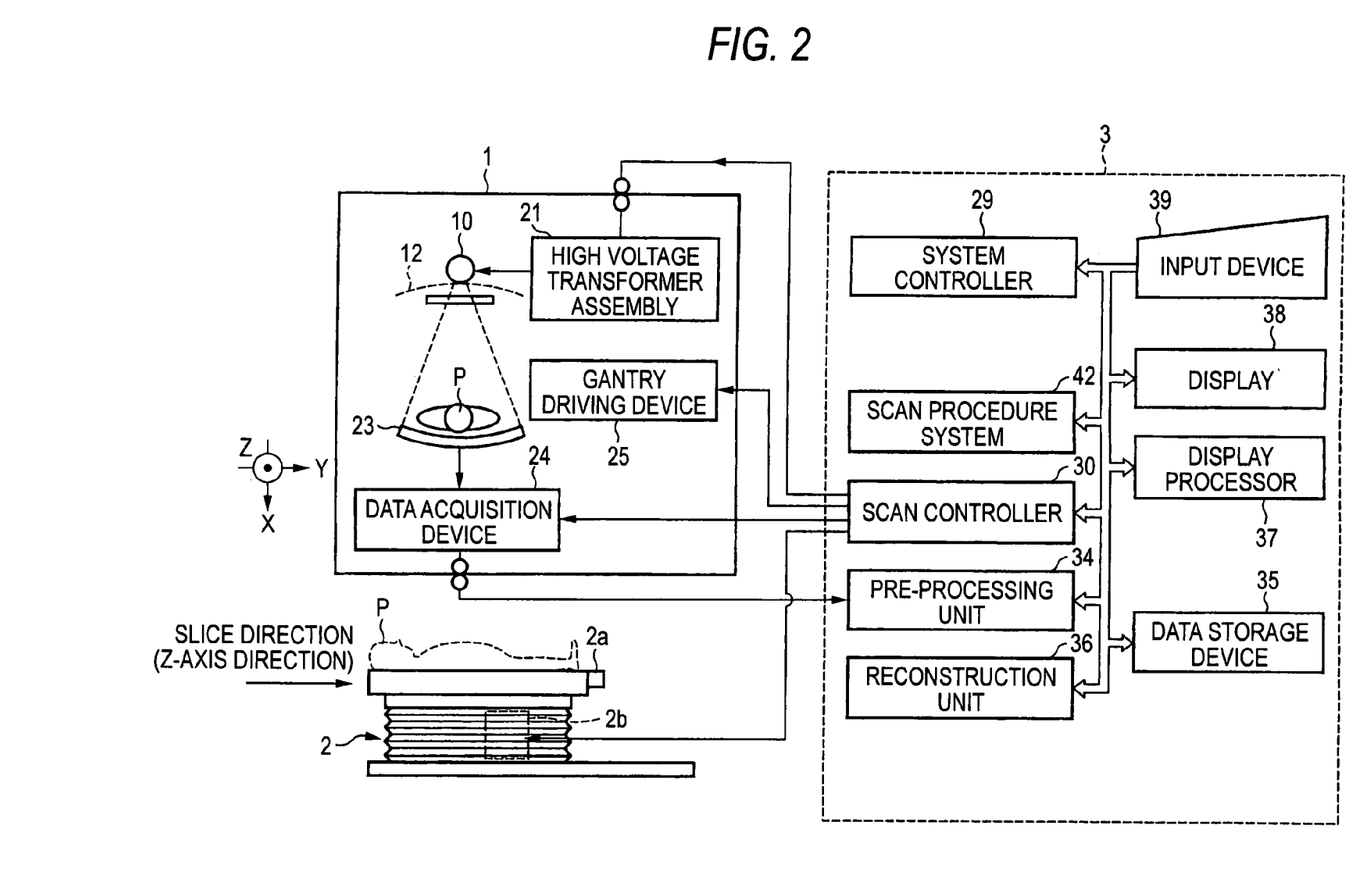
FIG. 2 is a view showing the configuration of an X-ray computed tomographic apparatus according to an embodiment of the invention.

FIG. 2 shows the configuration of the X-ray computed tomographic apparatus according to this embodiment. The X-ray computed tomographic apparatus includes a gantry 1 configured to acquire projection data related to the subject. The gantry 1 includes an X-ray tube 10 and an X-ray detector 23. Both the X-ray tube 10 and the X-ray detector 23 are mounted to a ring-shaped rotational frame 12, which is driven to rotate about the Z-axis by a gantry driving device 25. The rotational frame 12 is provided with an aperture at the center thereof, and the subject P laid on the tabletop 2a of the diagnostic table 2 is inserted into the aperture. A slit 22 used to vary the irradiation width of X-rays depending on the slice thickness is placed between the X-ray tube 10 and the aperture.

A tube voltage from a high voltage transformer assembly 21 is applied between the cathode and the anode of the X-ray tube 10, while a filament current from the high voltage transformer assembly 21 is supplied to the filament of the X-ray tube 10. X-rays are generated by the application of the tube voltage and the supply of the filament current.

Figure 3A:
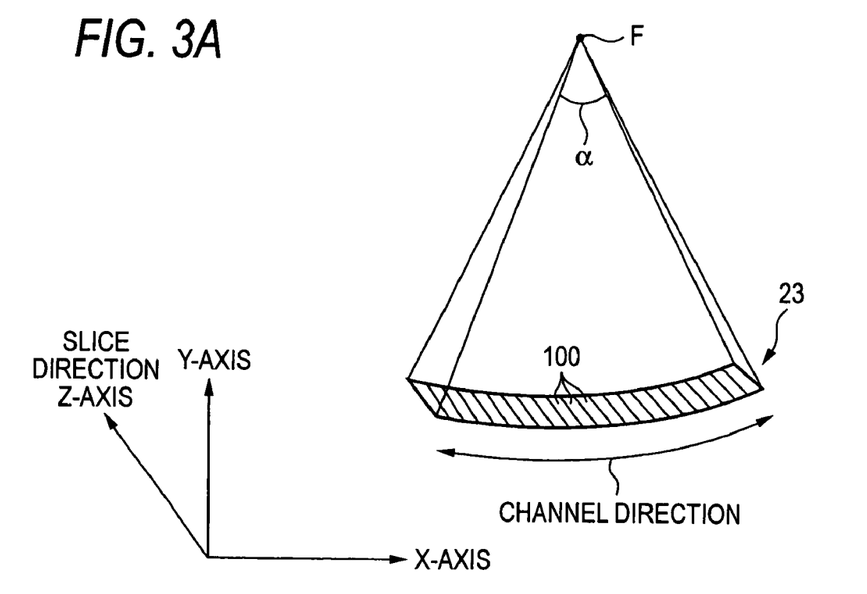
FIG. 3A and FIG. 3B are perspective views of an X-ray detector of FIG. 2.
Figure 3B:
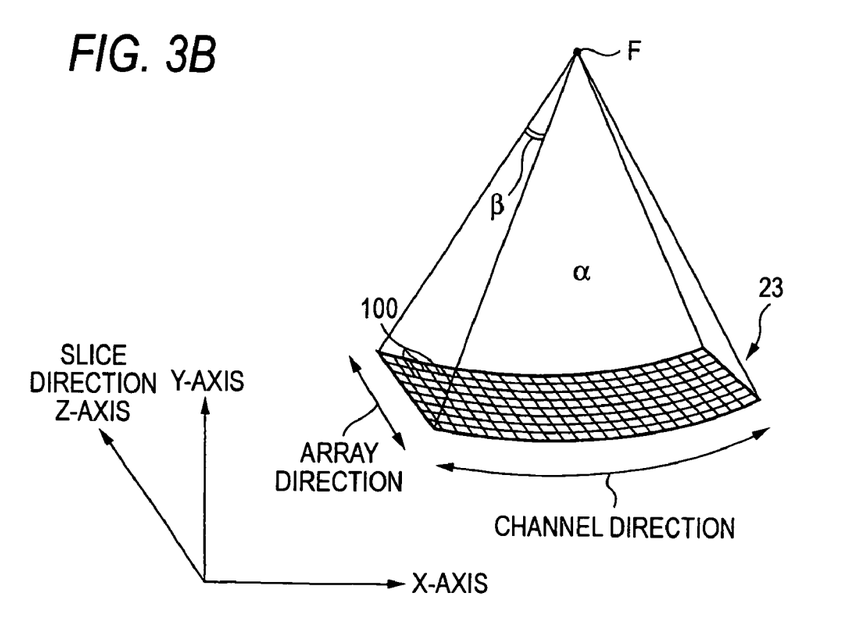

As is shown in FIG. 3A and FIG. 3B, the X-ray detector 23 includes plural X-ray detection elements 100 each having, for example, a 0.5 mm×0.5 mm tetragonal light-reception surface. In the case of FIG. 3A, for example, 916 X-ray detection elements 100 are aligned in an array along the channel direction. In the case of FIG. 3B, arrays of FIG. 3A are provided, for example, in 40 rows in parallel along the slice direction. The detector of FIG. 3A is referred to as the single-slice type, and the detector of FIG. 3B is referred to as the multi-slice type. The X-ray detector 23 can be of either type.

A data acquisition device 24, generally referred to as a DAS (data acquisition system), converts a signal in each channel outputted from the detector 23 to a voltage signal, amplifies the voltage signal, and converts the amplified voltage signal to a digital signal. Data (raw data) thus obtained is supplied to a computer unit 3 installed at the outside of the gantry. A pre-processing unit 34 of the computer unit 3 performs compensation processing, such as sensitivity compensation, on the raw data outputted from the data acquisition device 24, and outputs projection data. The projection data is then sent to and stored in a data storage device 35 of the computer system 3.

The computer system 3 comprises a system controller 29, an input device 39 provided with a keyboard, a mouse, etc., a display 38, a scan controller 30, a reconstruction unit 36, and a scan procedure system 42 in addition to the aforementioned pre-processing unit 34 and the storage device 35. The reconstruction unit 36 is able to selectively perform the reconstruction processing according to either of the followings: the typical fan-beam reconstruction method (also referred to as the fan-beam convolution back projection method); and a reconstruction method in a case where projection rays cross with the reconstruction plane like a cone beam, other than the helical interpolation that can be used together with the fan-beam reconstruction method in finding projection data on the reconstruction plane through interpolation from projection data of, for example, two rotations, the method including the Feldkamp method, known as an approximate image reconstruction method, by which convolution is performed by deeming the beam as a fan projection beam on the assumption that the cone angle is small and back projection is performed along rays at the time of scanning, and the cone-beam reconstruction method, known as a method capable of suppressing cone-angle induced errors compared with the Feldkamp method, by which projection data is compensated in response to the angle of rays with respect to the reconstruction plane.

Figure 4:
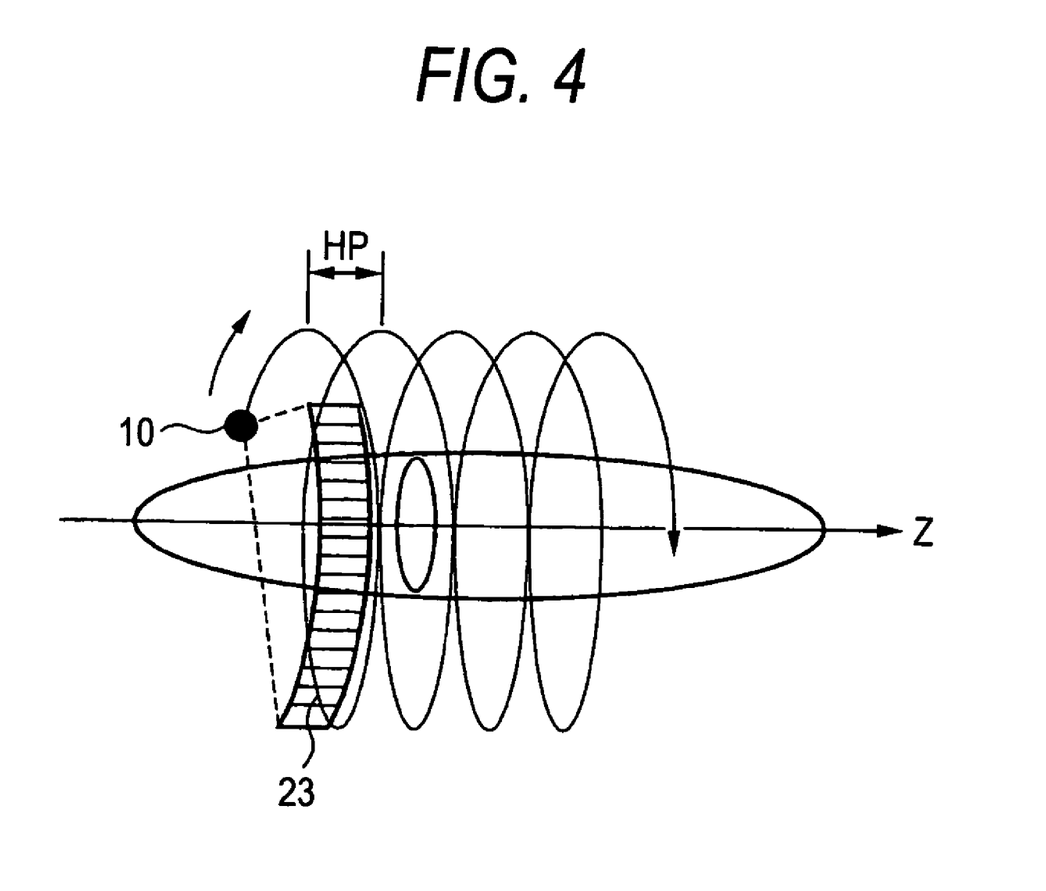
FIG. 4 is a view showing helical path of an X-ray tube of FIG. 2.

The scan procedure system 42 is provided to assist the operator in a work of determining the scan procedure, and constructs a scan procedure screen used to set scan conditions, such as a helical pitch (HP) indicating a distance the tabletop moves while the X-ray tube 10 rotates once as shown in FIG. 4, and a scan speed (SS) indicating a time needed for the X-ray tube 10 to rotate once.

Figure 5:
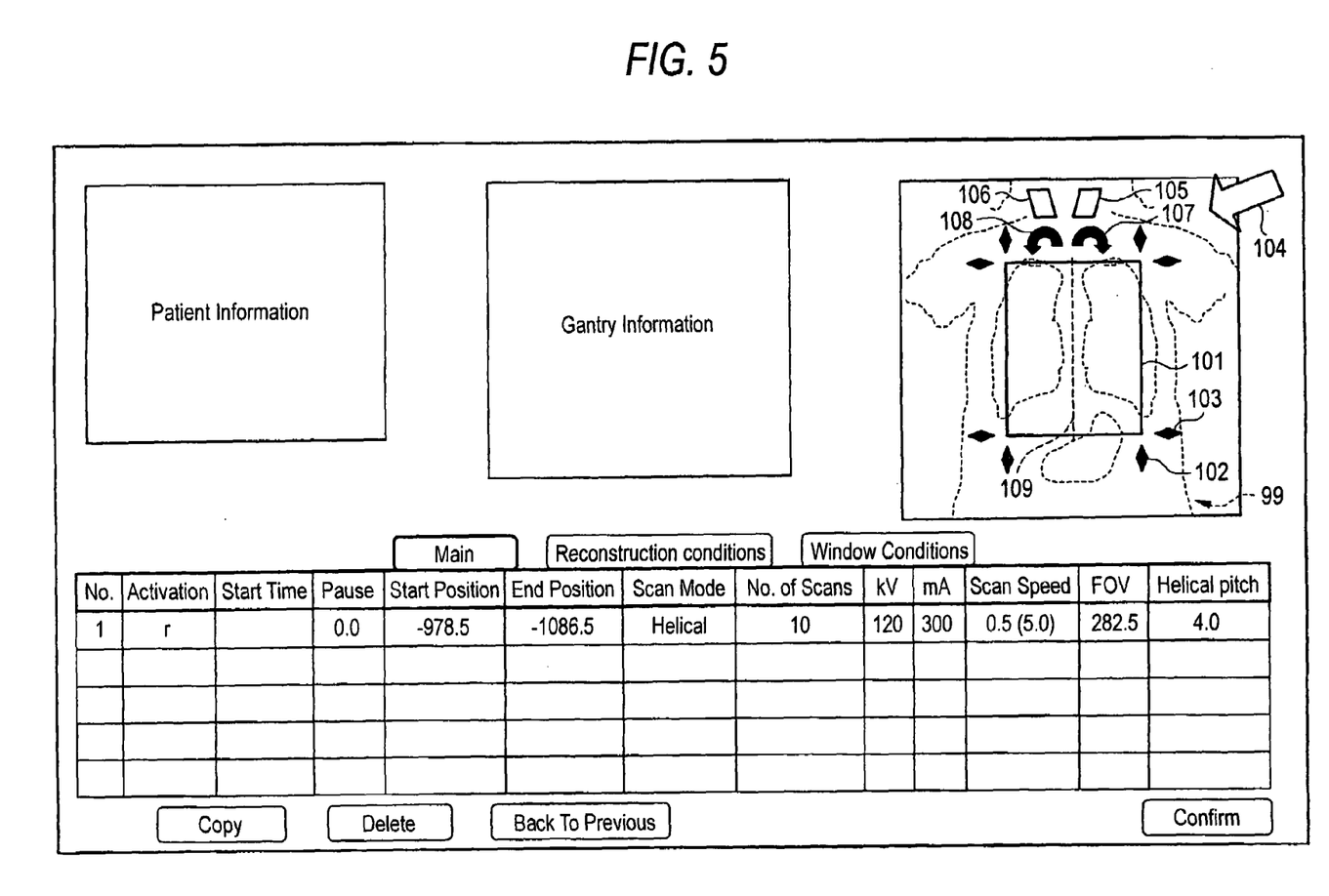
FIG. 5 is a view showing an example of a scan procedure screen constructed by a scan procedure system of FIG. 2.

FIG. 5 shows an example of the scan procedure screen. The scan procedure screen includes patient information, gantry information, and detailed information of the scan conditions at the bottom of the screen as well as a scanogram image 99. The scanogram image 99 is displayed in an orientation such that the Z-axis (the center of rotation) thereof is parallel to the vertical direction (possibly, the horizontal direction in some cases) of the screen. Thus, when scanogram imaging is performed while the body axis of the subject is tilted with respect to the Z-axis, the scanogram image 99 is displayed on the screen as being tilted with respect to the vertical direction of the screen as well.

The scan conditions include the activation (distinction between the manual trigger and the automatic trigger to start the scan), scan start time (start time), start position of helical scan, a pause between scans, end position of helical scan, scan mode (distinction among single-slice/multi-slice/helical), start position of scan, end position of scan, tube voltage kV, tube current mA, scan speed (time in parentheses indicates a time needed for the entire scans), the number of slices (the number of arrays used), helical pitch, reconstruction mode, and FOV (width of reconstruction range).

A quadrilateral frame line 101 specifying the reconstruction range is displayed on the scanogram image 99. A frame line, generally in a dotted line, specifying the scan range corresponding to the reconstruction range is displayed together with the frame line 101 specifying the reconstruction range in some cases. The quadrilateral frame line 101 specifying the reconstruction range is initially provided as an oblong with its center line 109 being parallel to the Z-axis (central axis of rotation).

Also, rhombic icons 102 for scaling up/down the range vertically and rhombic icons 103 for scaling up/down the range horizontally are displayed at the four corners of the frame line 101 specifying the reconstruction range, so that the operator is able to scale up/down the reconstruction range as needed by moving the pointer 104 to any of the icons 102 and 103 and dragging the pointer 104 with the use of, for example, the mouse of the input device 39. Also, the operator is able to move the reconstruction range in parallel vertically and/or horizontally by moving the pointer 104 on the frame line 101 and dragging the pointer 104 with the use of, for example, the mouse of the input device 39.

Figure 6:
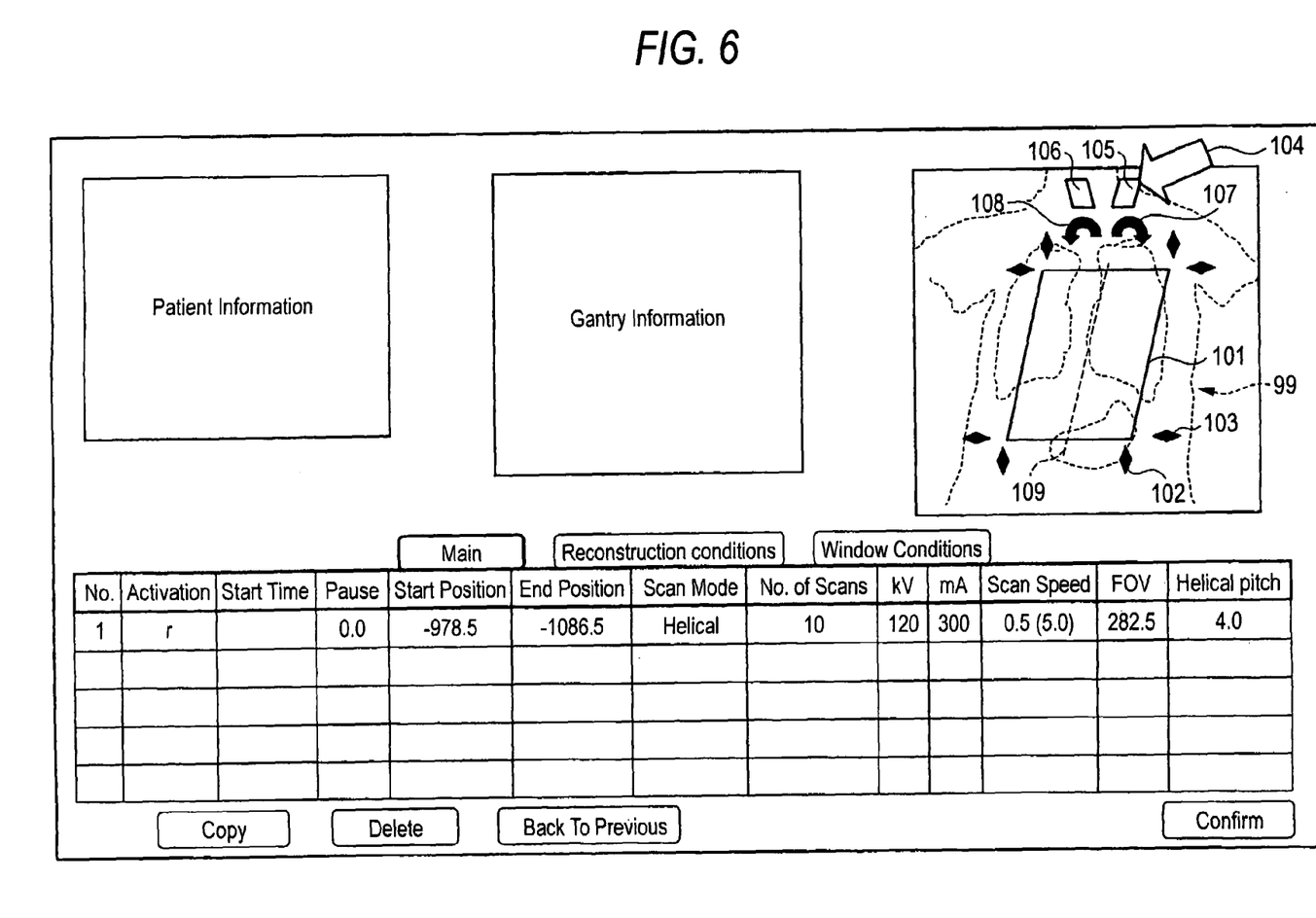
FIG. 6 is a view showing a frame line specifying a reconstruction range transformed with a click on a "transformation icon" of FIG. 5.

Further, on the scanogram image 99 are superposed transformation icons 105 and 106 and rotation icons 107 and 108. A transformation command is inputted with a click on the transformation icon 105. Upon input of the transformation command, as is shown in FIG. 6, the frame line 101 specifying the reconstruction range is transformed to a parallelogram. A degree of transformation, that is, a tilt of the center line 109 with respect to the vertical direction of the screen, is determined, for example, by the number of clicks. For instance, a tilt of 2.5° is given with one click. With a click on the other transformation icon 106, the frame line 101 specifying the reconstruction range is transformed in an opposite direction to the direction of FIG. 6. A degree of transformation is also determined by the number of clicks.

Figure 7:
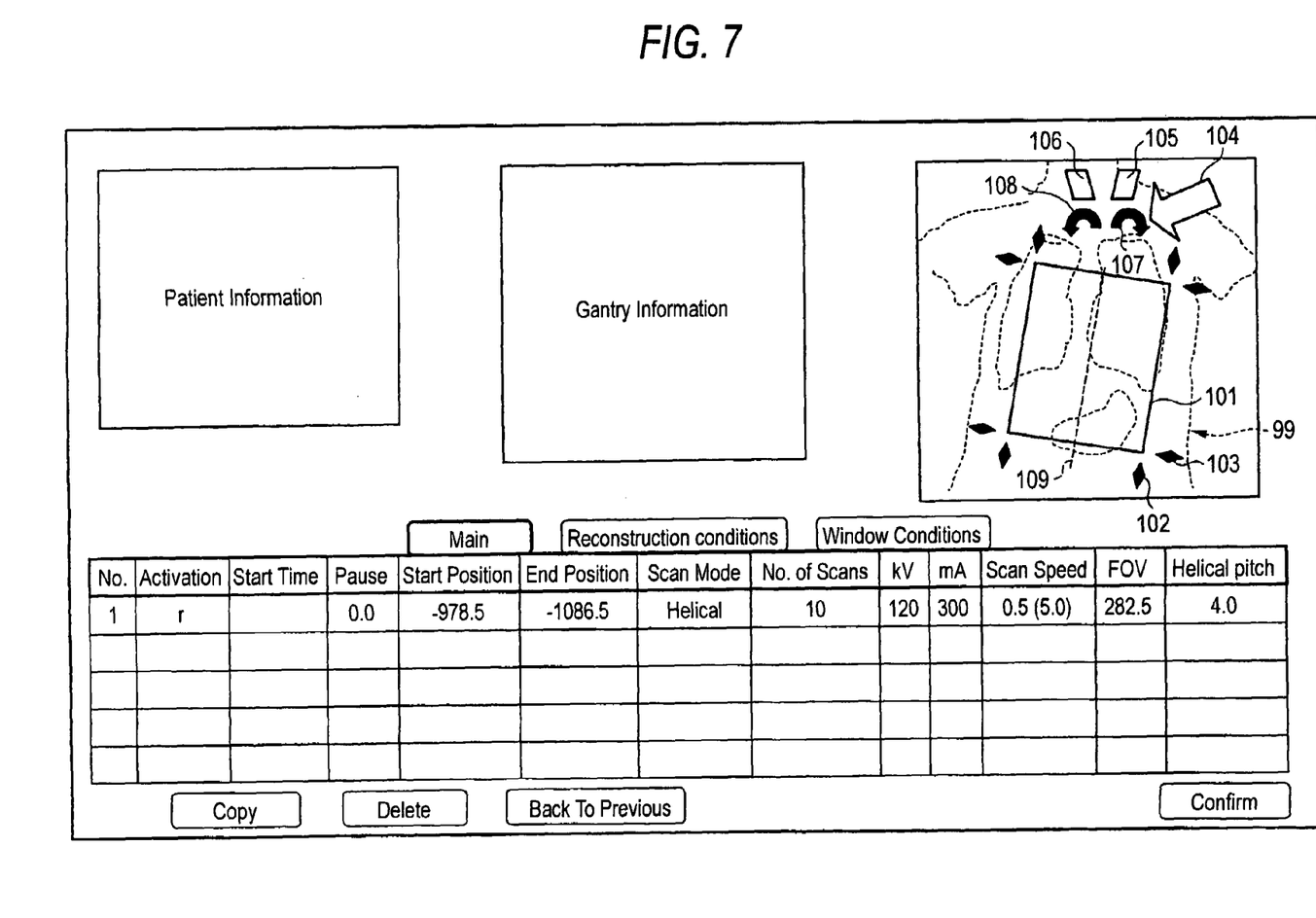
FIG. 7 is a view showing a frame line specifying a reconstruction range rotated with a click on a "rotation icon" of FIG. 5.

A rotation command is inputted with a click on the rotation icon 107. Upon input of the rotation command, as is shown in FIG. 7, the frame line 101 specifying the reconstruction range is rotated about its center. A degree of rotation, that is, a tilt of the center line 109 with respect to the vertical direction of the screen, is determined, for example, by the number of clicks. For instance, a rotation by 2.5° is given with one click. With a click on the other rotation icon 108, the frame line 101 specifying the reconstruction range is rotated in a direction opposite to the direction of FIG. 7. A degree of rotation is also determined by the number of clicks. Basically, transformation and rotation are performed alternatively.

As has been described, the scanogram image 99 is displayed in an orientation such that the Z-axis (center of rotation) thereof is parallel to the vertical direction of the screen. Thus, when scanogram imaging is performed while the subject is tilted with respect to the Z-axis, the tilt is reflected on the scanogram image 99 on the screen as are shown in FIG. 6 and FIG. 7.

The operator thus drags and moves the frame line 101 specifying the reconstruction range in parallel and clicks either the transformation icon 105 in the forward direction or the transformation icon 106 in the backward direction as many times as necessary, so that the center line 109 of the frame line 101 specifying the reconstruction range becomes parallel to and agrees as much as possible with the body axis of the subject on the tilted scanogram image 99. Also, the operator drags and moves the frame line 101 specifying the reconstruction range in parallel and clicks either the rotation icon 107 in the forward direction or the rotation icon 108 in the backward direction as many times as necessary, so that the center line 109 of the frame line 101 specifying the reconstruction range becomes parallel to and agrees as much as possible with the body axis of the subject assumed on the tilted scanogram image 99. Alternatively, it may be possible to transform and rotate the frame line 101 specifying the reconstruction range with the use of the transformation icon 105 or 106 together with the rotation icon 107 or 108.

Figure 8A:
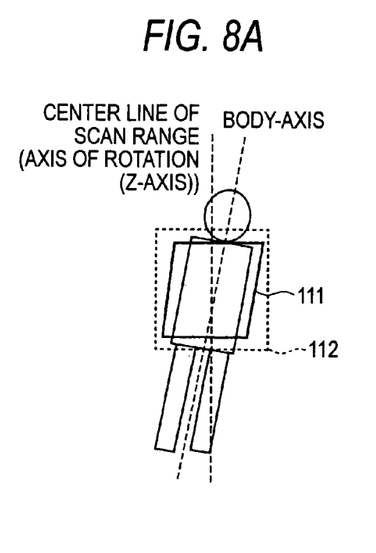
FIG. 8A, FIG. 8B, and FIG. 8C are views used to explain reconstruction processing corresponding to the transformed reconstruction range of FIG. 6.

There is a slight difference between the examples of FIG. 6 and FIG. 7 in terms of image reconstruction. When the frame line 101 specifying the reconstruction range is transformed as shown in FIG. 6, the scan procedure system 42 determines, as is shown in FIG. 8A, the reconstruction range 111 to correspond to the frame line 101, and determines the scan range 112 to correspond to the reconstruction range 111. The scan range 112 is set to the shape of a cylindrical column whose longitudinal cross section is an oblong having the Z-axis (axis of rotation) at the center and covering the reconstruction range 111.

Figure 8B:
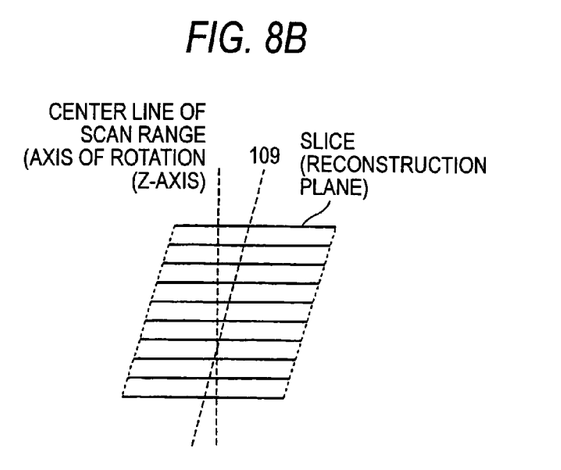

As is shown in FIG. 8B, the reconstruction unit 36 extracts projection data corresponding to respective slices from projection data acquired by scans, and reconstructs image data on the basis of the projection data thus extracted. Widths of the respective slices are set according to the horizontal width of the frame line 101 specifying the reconstruction range, and the centers of the respective slices are set on the center line 109 of the frame line 101 specifying the reconstruction range. Because the center line 109 of the reconstruction range is set with a tilt with respect to the center line of the scan range, the horizontal positions of the respective slices, that is, a distance from the center line of the scan range to the center of each slice, vary from slice to slice. However, the centers of the respective slices are all placed on the body axis of the subject.

Figure 8C:
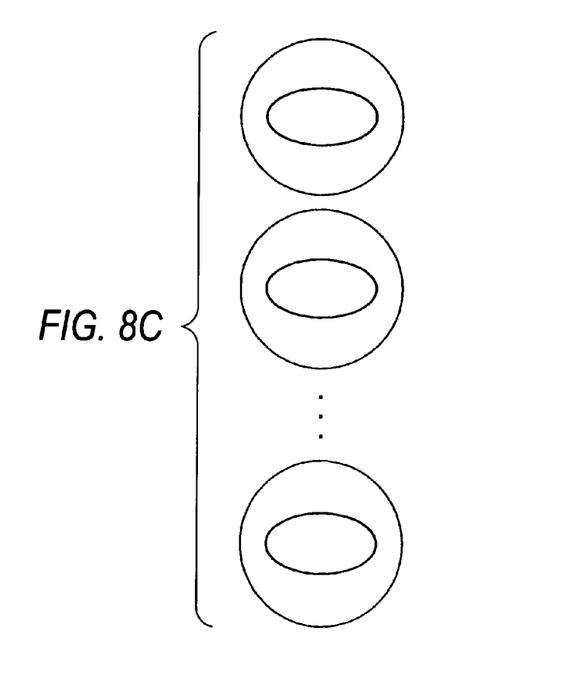

Because the center of the slice can be set for each slice in response to the tilted body position of the subject in the manner descried above, even when scans are performed while the body axis of the subject is titled with respect to the Z-axis, the body axis of the subject can be positioned on almost the center of the image as shown in FIG. 8C. This eliminates offset between the position on the image and the position on the subject, which makes observation quite easy. Also, by converting a horizontal distance of the subject to an actual distance on the basis of the tilt of the frame line 101, it is possible to reduce errors in measurement of a distance or a volume.

Figures 9A, 9B, 9C:
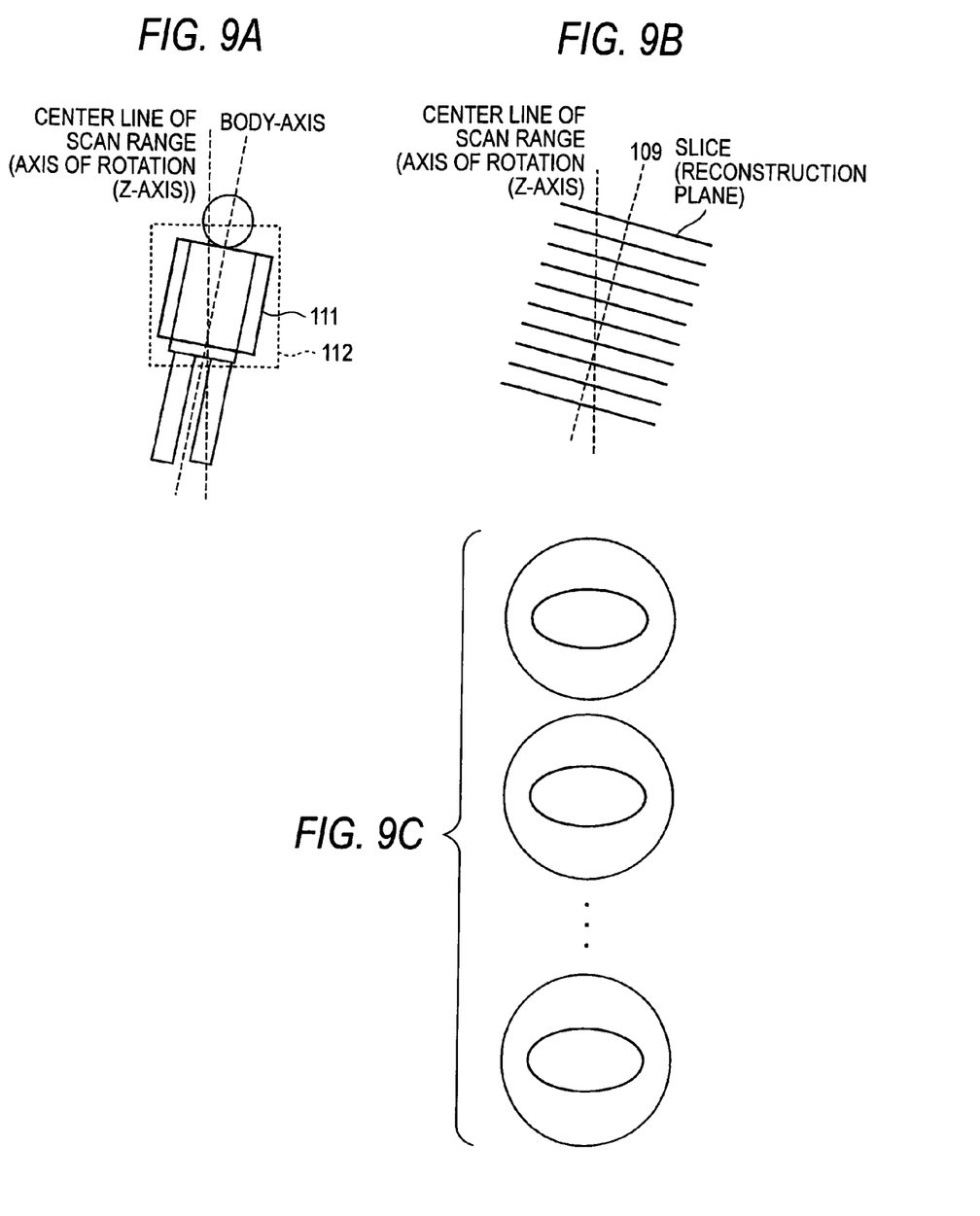
FIG. 9A, FIG. 9B, and FIG. 9C are views used to explain reconstruction processing corresponding to the rotated reconstruction range of FIG. 7.

Then, in a case where the frame line 101 specifying the reconstruction range is rotated as shown in FIG. 7, the scan procedure system 42 determines, as is shown in FIG. 9A, the reconstruction range 111 corresponding to the frame line 101 together with the scan range 112. In this case, the scan range 112 is set to the shape of a cylindrical column whose longitudinal cross section is an oblong having the Z-axis (axis of rotation) at the center and covering the reconstruction range 111.

Figure 10A:
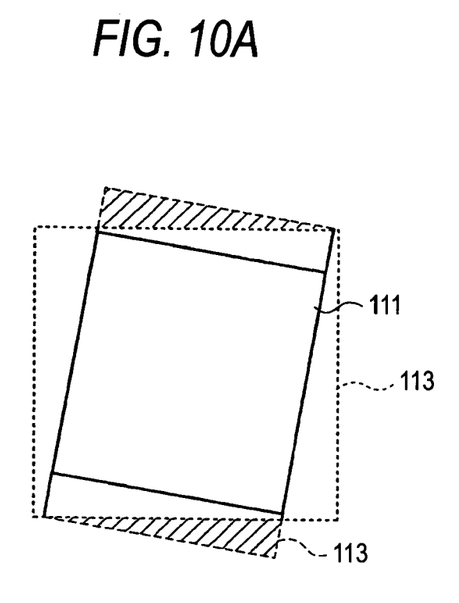
FIG. 10A and FIG. 10B are views showing two types of scan range corresponding to the rotated reconstruction range of FIG. 7.
Figure 10B:
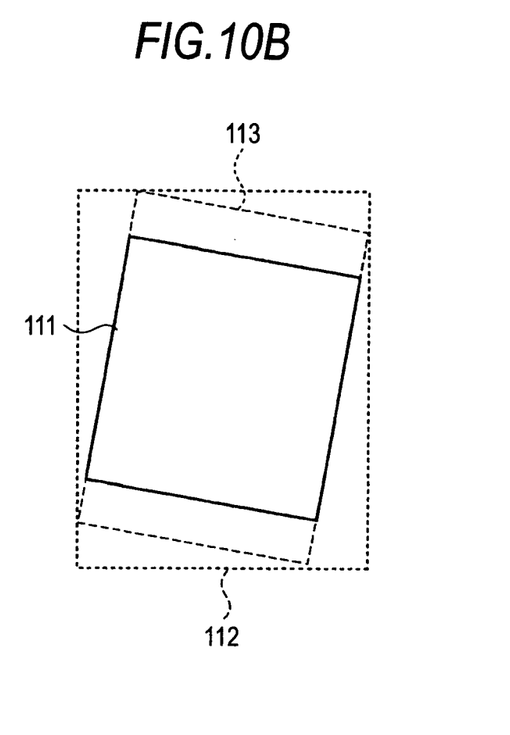

The scan range 112 can be selected from the range shown in FIG. 10A and the range shown in FIG. 10B wider than the one shown in FIG. 10A. In the helical reconstruction, as is known, projection data at the slice position is generated through interpolation from projection data of two, preceding and following rotations. In other words, the helical reconstruction needs projection data that covers a wider range 113, which is wider than the outermost slice within the reconstruction range 111 to the outside by at least one rotation. FIG. 10B shows an example when the scan range 112 is set to acquire the entire projection data of this wider range 113. In contrast, FIG. 10A shows an example of a narrow scan range 112, in which part of projection data shaded by diagonal lines is replenished through extrapolative interpolation. The operator may make a selection between these two types, or the selection may be made automatically depending on the various conditions of the region to be imaged.

As is shown in FIG. 9B, the reconstruction unit 36 reconstructs image data by either the cone-beam reconstruction method or the tilt reconstruction method for each of plural slices (reconstruction planes) orthogonal to the center line 109 of the reconstruction range rotated in response to a tilt of the body axis of the subject, on the basis of the projection data acquired by scans. In other words, the pixel value of each pixel within the slice tilted with respect to the central axis of the scan range is computed as a filter integral value of projection data of plural X-ray paths that cross with the each pixel diagonally.

The width of each slice is set according to the width of the frame line 101 specifying the reconstruction range, and the center of each slice is set on the center line 109 of the frame line 101 specifying the reconstruction range. Because the center line 109 of the reconstruction range is set with a tilt with respect to the center line of the scan range, the horizontal positions of the respective slices, that is, a distance from the center line of the scan range to the center of each slice, vary from slice to slice.

Because the center of the slice can be set for each slice in response to the titled body position of the subject in the manner described above, even when scans are performed while the body axis of the subject is tilted with respect to the Z-axis, the body axis of the subject can be positioned on almost the center of the image as is shown in FIG. 9C. Moreover, in this example, an image of a plane orthogonal to the body axis of the subject can be obtained, which reduces errors in horizontal distance associated with a tilt of the body axis with respect to the Z-axis. In short, it is possible to substantially eliminate a state where the body axis of the subject is tilted with respect to the Z-axis. Because errors in distance can be eliminated not only vertically but also horizontally, errors can be reduced in measurement of a distance or a volume; moreover, MPR (multi-planar reconstruction) processing or 3-D processing can be performed directly without the need for special compensation processing.

The invention can be applied to, for example, PET (Positron Emission computed Tomography), as an image diagnosis apparatus of a type that reconstructs a planar image on the basis of the subject's data acquired in many directions, as with the X-ray computed tomographic apparatus.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An X-ray computed tomographic apparatus, comprising:
    a display portion to display, on a screen, a scanogram related to a subject together with a quadrilateral frame line specifying a reconstruction range;
    an input portion to input a command to transform the frame line specifying said reconstruction range to a parallelogram or rotate the frame line specifying said reconstruction range;
    a scan portion to perform scanning in a scan range corresponding to said reconstruction range; and
    a reconstruction portion to reconstruct image data related to plural slices, parallel to one another and included in said reconstruction range, slice-by-slice on the basis of projection data acquired by said scanning.

2. The X-ray computed tomographic apparatus according to claim 1, wherein:
    a center line of said transformed or rotated reconstruction range is tilted with respect to a center line of said scan range.

3. The X-ray computed tomographic apparatus according to claim 2, wherein:
    a distance from the center line of said scan range to a center of each of said plural slices varies from slice to slice.

4. The X-ray computed tomographic apparatus according to claim 2, wherein:
    said slices are tilted with respect to the center line of said transformed reconstruction range.

5. The X-ray computed tomographic apparatus according to claim 4, wherein:
    said slices are orthogonal to the center line of said scan range.

6. The X-ray computed tomographic apparatus according to claim 2, wherein:
    said slices are orthogonal to the center line of said rotated reconstruction range.

7. The X-ray computed tomographic apparatus according to claim 6, wherein:
    said slices are tilted with respect to the center line of said scan range.

8. The X-ray computed tomographic apparatus according to claim 1, wherein:
    an icon corresponding to transformation or rotation is displayed in the vicinity of the frame line specifying said reconstruction range.

9. The X-ray computed tomographic apparatus according to claim 1, wherein:
    said scan range is set to a shape of a cylindrical column whose longitudinal cross section is an oblong having an axis of rotation at a center and covering said transformed or rotated reconstruction range.

10. The X-ray computed tomographic apparatus according to claim 1, wherein:
    said scan range covers said transformed or rotated reconstruction range.

11. The X-ray computed tomographic apparatus according to claim 10, wherein:
    said scan range has a length longer than said transformed or rotated reconstruction range with respect to a direction parallel to a central axis thereof.

12. The X-ray computed tomographic apparatus according to claim 10, wherein:
    said scan range has a width almost equal to said transformed or rotated reconstruction range with respect to a direction orthogonal to a central axis thereof.

13. A method for X-ray computed tomography, comprising:
    displaying, on a screen, a scanogram related to a subject together with a quadrilateral frame line specifying a reconstruction range;
    inputting a command to transform the frame line specifying said reconstruction range to a parallelogram or rotate the frame line specifying said reconstruction range;
    performing scanning in a scan range corresponding to said reconstruction range; and
    reconstructing image data related to plural slices, parallel to one another and included in said reconstruction range, slice-by-slice on the basis of projection data acquired by said scanning.

14. The method for X-ray computed tomography according to claim 13, wherein:
    a center line of said transformed or rotated reconstruction range is tilted with respect to a center line of said scan range.

15. The method for X-ray computed tomography according to claim 14, wherein:
    a distance from the center line of said scan range to a center of each of said plural slices varies from slice to slice.

16. The method for X-ray computed tomography according to claim 14, wherein:
    said slices are tilted with respect to the center line of said transformed reconstruction range.

17. The method for X-ray computed tomography according to claim 16, wherein:

said slices are orthogonal to the center line of said scan range.

18. The method for X-ray computed tomography according to claim 14, wherein:
said slices are orthogonal to the center line of said rotated reconstruction range.

19. The method for X-ray computed tomography according to claim 18, wherein:
said slices are tilted with respect to the center line of said scan range.

20. The method for X-ray computed tomography according to claim 13, wherein:
an icon corresponding to transformation or rotation is displayed in the vicinity of the frame line specifying said reconstruction range.

21. The method for X-ray computed tomography according to claim 13, wherein:
said scan range is set to a shape of a cylindrical column whose longitudinal cross section is an oblong having an axis of rotation at a center and covering said transformed or rotated reconstruction range.

22. The method for X-ray computed tomography according to claim 13, wherein:
said scan range covers said transformed or rotated reconstruction range.

23. The method for X-ray computed tomography according to claim 22, wherein:
said scan range has a length longer than said transformed or rotated reconstruction range with respect to a direction parallel to a central axis thereof.

24. The method for X-ray computed tomography according to claim 22, wherein:
said scan range has a width almost equal to said transformed or rotated reconstruction range with respect to a direction orthogonal to a central axis thereof.

* * * * *